US005731158A

United States Patent [19]
Bobrow et al.

[11] Patent Number: 5,731,158
[45] Date of Patent: Mar. 24, 1998

[54] CATALYZED REPORTER DEPOSITION

[75] Inventors: Mark Norman Bobrow, Woburn; Gerald Joseph Litt, Wellesley, both of Mass.

[73] Assignee: E. I. du Pont de Nemours and Company, Wilmington, Del.

[21] Appl. No.: 651,012

[22] Filed: May 20, 1996

Related U.S. Application Data

[62] Division of Ser. No. 238,186, May 4, 1994, Pat. No. 5,583,001, which is a continuation of Ser. No. 914,374, Jul. 15, 1992, abandoned, which is a division of Ser. No. 589,719, Sep. 28, 1990, Pat. No. 5,196,306, which is a continuation-in-part of Ser. No. 330,357, Mar. 29, 1989, abandoned, and a continuation-in-part of Ser. No. 494,226, Mar. 20, 1990, abandoned.

[51] Int. Cl.$^6$ .................................................. G01N 33/53
[52] U.S. Cl. .................. 435/7.5; 435/7.1; 435/7.71; 435/7.72; 435/7.9; 435/7.91; 435/15; 435/18; 435/21; 435/25; 435/28; 436/501; 436/518
[58] Field of Search ................. 435/7.1, 7.5, 7.6, 435/7.7, 7.71, 7.72, 7.8, 7.9, 7.91, 15, 18, 21, 25, 28; 436/501, 518

[56] References Cited

U.S. PATENT DOCUMENTS

| | | | |
|---|---|---|---|
| 4,128,629 | 12/1978 | Eldred et al. | 424/1 |
| 4,228,237 | 10/1980 | Hevey et al. | 435/5 |
| 4,290,916 | 9/1981 | Litman et al. | 435/6 |
| 4,299,916 | 11/1981 | Litman et al. | 435/6 |
| 4,318,899 | 3/1982 | Mayol | 424/1 |
| 4,318,980 | 3/1982 | Boguslaski et al. | 435/7 |
| 4,376,825 | 3/1983 | Rubenstein et al. | 435/188 |
| 4,391,904 | 7/1983 | Litman et al. | 435/7 |
| 4,463,090 | 7/1984 | Harris | 435/7 |
| 4,466,951 | 8/1984 | Pittman | 424/1.1 |
| 4,598,042 | 7/1986 | Self | 435/7 |
| 4,668,621 | 5/1987 | Doellgast | 435/13 |
| 4,687,735 | 8/1987 | Dinello et al. | 435/7 |
| 4,745,054 | 5/1988 | Rabin et al. | 435/6 |
| 4,859,583 | 8/1989 | Heller et al. | 435/7 |
| 4,904,583 | 2/1990 | Mapes et al. | 435/7.92 |
| 4,999,284 | 3/1991 | Ward et al. | 435/4 |
| 5,196,306 | 3/1993 | Bobrow et al. | 434/7.9 |

FOREIGN PATENT DOCUMENTS

| | | |
|---|---|---|
| 0123265 | 10/1984 | European Pat. Off. . |
| 0144744 | 6/1985 | European Pat. Off. . |
| 181762 | 5/1986 | European Pat. Off. . |
| 1401297 | 7/1975 | United Kingdom . |
| 2059421 | 4/1981 | United Kingdom . |
| WO81/00725 | 3/1981 | WIPO . |
| 8402193 | 6/1984 | WIPO ........................ G01N 35/54 |
| WO84/02193 | 6/1984 | WIPO . |

OTHER PUBLICATIONS

ELAST™ ELISA Amplification System, Instruction Manual, 060391, Du Pont/NEN Research Products.
BLAST™ Blotting Amplification System, Instruction Manual, 110191, Du Pont/NEN Research Products.
Lowry et al., Journal of Biological Chemistry, pp. 2746–2755, vol. 236, No. 10 (Oct. 1961).
Vary et al., Clinical Chemistry, pp. 1696–1701, vol. 32 (1986).
Bobrow et al., J. Immunological Methods, vol. 125, pp. 279–285 (1989).
D. L. Bates, Trends in Biotechnology, pp. 204–209, vol. 5, No. 7 (1987).
Doellgast et al., Analytical Biochemistry, pp. 529–534, vol. 147 (1985).
Doellgast et al., Analytical Biochemistry, pp. 199–207, vol. 152 (1986).
Doellgast et al., Analytical Biochemistry, pp. 102–114, vol. 162 (1987).
Doellgast et al., Analytical Biochemistry, pp. 97–105, vol. 167 (1987).
Doellgast et al., Clin. Chem., pp. 294–299, vol. 34, No. 2 (1988).
Bobrow et al, 1989, Catalyzed, Reporter deposition J Immunol. Meth. 125:279–285.
Bates, 1987, Enzyme amplification in diagnostic Trends in Biotechnol 5:204–209.
Dorland's Illustrated Medical Dictionary. Philadelphia: Saunders, 1985, pp. 1130–1131.
Tijssen. *Laboratory Techniques in Biochemistry and Molecular Biology: Practice and Theory of Enzyme Immunoassays*, vol. 15 (New York, Elsevier, 1985). pp. 9–20.

*Primary Examiner*—Donald E. Adams
*Assistant Examiner*—Jeffrey Stucker

[57] ABSTRACT

The present invention concerns a method to catalyze reporter deposition to improve detection or quantitation of an analyte in a sample by amplifying the detector signal which comprises reacting an analyte dependent enzyme activation system with a conjugate consisting of a detectably labeled substrate specific for the enzyme system, said conjugate reacts with the analyte dependent enzyme activation system to form an activated conjugate which deposits substantially wherever receptor for the activated conjugate is immobilized, said receptor not being reactive with the analyte dependent enzyme activation system.

In another embodiment the invention concerns an assay for detecting or quantitating the presence or absence of an analyte in a sample using catalyzed reporter deposition to amplify the reporter signal.

16 Claims, 7 Drawing Sheets

CATALYZED REPORTER DEPOSITION

RELATED APPLICATIONS

This is a division of application Ser. No. 08/238,186, filed May 4, 1994 issued as U.S. Pat. No. 5,583,001, which is a continuation of application Ser. No. 07/914,374 filed Jul. 15, 1992, now abandoned which is a division of application Ser. No. 07/589,719 filed Sep. 28, 1990 issued as U.S. Pat. No. 5,196,306 on Mar. 23, 1993, which is a continuation-in-part of application Ser. No. 07/330,357, filed Mar. 29, 1989, now abandoned, and application Ser. No. 07/494,226, filed Mar. 20, 1990, now abandoned.

FIELD OF THE INVENTION

This invention relates to assays and, more particularly, to catalyzing reporter deposition via an activated conjugate to amplify the detector signal thereby improving detection and/or quantitation of an analyte in a sample.

BACKGROUND OF THE INVENTION

The introduction of immunodiagnostic assays in the 1960s and 1970s greatly increased the number of analytes amenable to precise and accurate measurement. Radioimmunoassays (RIAs) and immunoradiometric (IRMA) assays utilize radioisotopic labeling of either an antibody or a competing antigen to measure an analyte. Detection systems based on enzymes or fluorescent labels were developed as an alternative to isotopic detection systems. Enzyme based assays proved to be more sensitive, faster, and less dependent upon expensive, sophisticated instrumentation.

The need for diagnostic assays having simpler formats, increased sensitivity with less dependence upon sophisticated and expensive instrumentation prompted investigators to try to harness the catalytic power of enzymes to develop these newer assays.

D. L. Bates, Trends in Biotechnology, pages 204–209, Vol. 5 No. 7 (1987), describes diagnostics which use a method of enzyme amplification to develop more sensitive and simple immunoassays. In this method a second enzyme system is coupled to the primary enzyme label, e.g., the primary enzyme can be linked catalytically to an additional system such as a substrate cycle or an enzyme cascade. Thus, the essence of enzyme amplification according to Bates is the coupling of catalytic processes wherein an enzyme is modulated by the action of a second enzyme, either by direct modification or by interaction with the product of the controlling enzyme.

U.S. Pat. No. 4,668,621, issued to Doellgast on May 26, 1987, describes application of an enzyme-linked coagulation assay (ELCA) to develop an amplified immunoassay using the clotting cascade to enhance sensitivity of detection of immune complexes. The process involves clot formation due to thrombin activated fibrin formation from insolubilized fibrinogen and labeled solubilized fibrinogen. Amplification of the amount of reportable ligand attached to solid phase is obtained only by combining use of clotting factor conjugates with subsequent coagulation cascade reactions. One of the disadvantages of this system is that it can only be used to measure the presence of materials which modulate the activity of one or more of the blood clotting factors. Another disadvantage is that the primary enzyme, thrombin, cannot be immobilized or coupled to a reporter or a member of a specific binding pair.

U.S. Pat. No. 4,463,090, issued to Harris on Jul. 31, 1984, describes a cascade amplification immunoassay requiring a combination of at least two sequential catalyses wherein a first enzyme activates a second enzyme which in turn acts upon the substrate.

Another amplification system is described in U.S. Pat. No. 4,598,042, issued to Self on Jul. 1, 1986, and U.K. Patent Application No. 2,059,421 which was published on Apr. 23, 1981, which disclose an immunoassay using an enzyme label to produce directly or indirectly a substance that is capable of influencing a catalytic event without itself being consumed during the catalytic event. More specifically, a primary enzyme system produces or removes a substance capable of modulating a secondary enzyme system which results in amplification. The enzyme systems use unconjugated enzymes to avoid the tendency to inactivate certain enzymes on conjugation.

European Patent Application Publication No. 123,265 which was published on Oct. 31, 1984, describes another cascade amplification immunoassay wherein a zymogen-derived-enzyme is coupled to a zymogen-to-enzyme cascade reaction sequence to obtain multiple stages of amplification in producing detectable marker material used to quantify analyte amount.

European Patent Application Publication No. 144,744, published Jun. 19, 1985, describes a specific binding assay based on enzyme cascade amplification wherein the label component employed in the detectant reagent is a participant in or a modulator of an enzyme cascade reaction wherein a first enzyme acts on a first substrate to product a second enzyme. The production of the second enzyme can be followed or the second enzyme can act on a second substrate to produce a third enzyme.

Similarly, U.S. Pat. No. 4,318,980, issued to Boguslaski et al. on Mar. 9, 1982, describes a heterogenous specific binding assay using a conjugate formed of a specific binding substance coupled to the reactant, i.e., an enzymatic reactant. The ability of the reactant to participate in the monitoring reaction to detect the presence of analyte is altered by the presence of the ligand in the medium. Thus, the conjugate in its free state is more active in the monitoring reaction than in its bound state.

A heterogenous specific binding assay using enzyme amplification is described in British Patent Application No. 1,401,297 which was published on Jul. 30, 1975 and U.S. Pat. No. 4,376,825, issued to Rubenstein et al. on Mar. 15, 1983. Amplification is achieved by bonding the compound to be assayed or a counterfeit of it to an enzyme. The resulting enzyme-bound-ligand competes with free ligand for specific receptor sites. When the enzyme-bound ligand is displaced by the free ligand the enzyme is then free to react with a large number number of substrate molecules and the concentration of the remaining substrate or of the product can be measured. PCT International Publication No. WO 81/00725 which was published on Mar. 19, 1981 describes a method of determining a substrate in a sample which comprises converting the substrate to a product in a first stage of a cyclic reaction sequence and converting the product back to the substrate in a second reaction stage of the cyclic reaction sequence. At least one of the first and second reaction stages is enzyme catalyzed.

PCT Application having International Publication Number WO 84/02193, which was published on Jun. 7, 1984, describes a chromgenic support immunoassay wherein the analyte is contacted with an enzyme-labeled antibody and in which the signal generated by the reaction of the enzyme with its substrate is concentrated on an active support.

European Patent Application Publication No. 181,762, published on May 21, 1986, describes a method to determine enzymatic activity in a liquid sample by particle agglutination or inhibition of particle agglutination.

Substrate/cofactor cycling is another example of amplification which is based on the cycling of a cofactor or substrate which is generated by the primary enzyme label. The primary enzyme converts the primary substrate to an active form which can be cycled by two enzymes of the amplifier cycle. These two enzymes are provided in high concentration and are poised to turn over high concentrations of substrate but are prevented from so doing until the cycling substrate is formed. The product of the primary enzyme is a catalytic activator of the amplifier cycle which responds in proportion to the concentration of substrate and hence the concentration of the enzyme label.

In the early sixties, Lowry et al., Journal of Biological Chemistry, pages 2746–2755, Vol. 236, No. 10 (October 1961), described the measurement of pyridine nucleotides by enzymatic cycling in which the coenzyme to be determined was made to amplify an enzymatic dismutation between two substrates.

A more complex substrate cycling system is described in U.S. Pat. No. 4,745,054, issued to Rabin et al. on May 17, 1988. The Rabin system involves using a small enzymically inactive peptide fragment of an enzyme as a label and conjugated with the complementary fragment to form an enzyme which catalyzes a primary reaction whose product is, or leads to, an essential coenzyme or prosthetic group for a second enzyme which catalyzes a secondary reaction leading to a detectable result indicating the presence of analyte.

Vary et al., Clinical Chemistry, pages 1696–1701, Vol. 32 (1986) describe an amplification method suited to nucleic acids. This is the strand displacement assay which uses the unique ability of a polynucleotide to act as a substrate label which can be released by a phosphorylase.

SUMMARY OF THE INVENTION

The present invention concerns a method to catalyze reporter deposition to improve detection or quantitation of an analyte in a sample by amplifying the detector signal which comprises reacting an analyte dependent enzyme activation system with a conjugate consisting of a detectably labeled substrate specific for the enzyme system, said conjugate reacts with the analyte dependent enzyme activation system to produce an activated conjugate which deposits substantially wherever receptor for the activated conjugate is immobilized, said receptor not being reactive with the analyte dependent enzyme activation system.

In another embodiment the invention concerns an assay for detecting or quantitating the presence or absence of an analyte in a sample using catalyzed reporter deposition to amplify the reporter signal.

DETAILED DESCRIPTION OF THE INVENTION

Figure 1:
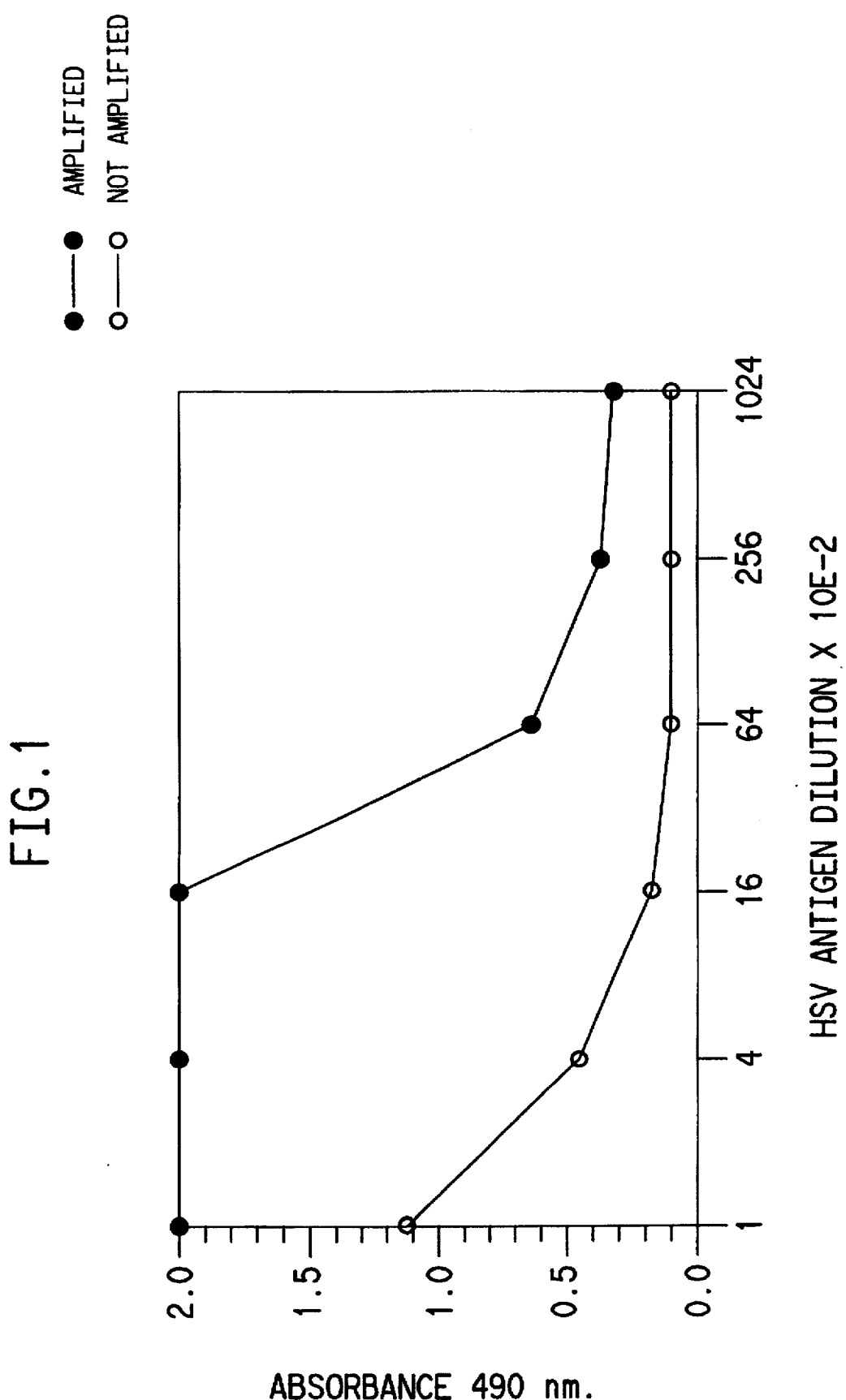
FIG. 1 is a graph comparing results of an HSV antigen assay run with and without catalyzed reporter deposition.

The term analyte dependent enzyme activation system (ADEAS) refers to an enzyme system wherein (i) at least one enzyme is coupled, in any manner known to those skilled in the art, to a member of a specific binding pair, or (ii) the enzyme need not be coupled to a member of a specific binding pair when it is the analyte. The enzyme, either by itself or in connection with a second enzyme, catalyzes the formation of an activated conjugate which then is deposited wherever a receptor for the activated conjugate is immobilized.

The term amplification as used herein means amplification of reporter signal due to deposition of a conjugate activated by an ADEAS.

The term conjugate means a detectably labeled substrate specific for the ADEAS whether it be a single enzyme ADEAS or multi-enzyme ADEAS. The substrate must have at least one component but is not limited to such. For example, the substrate can consist of two components. One component contains the binding site for the receptor and is detectably labeled. The other component is a constituent which prevents or interferes with binding to the receptor until such time as the ADEAS primes the conjugate as is discussed below. Another example of a conjugate is biotin-tyramine wherein tyramine is the substrate portion and biotin constitutes the detectable label as described below. Conjugates are described in greater detail below as well.

The term detectably labeled means that the substrate can be coupled to either a reporter or to an unlabeled first member of a specific binding pair provided that the reporter introduces a different moiety to the substrate as is discussed below. When the substrate is coupled to an unlabeled member of a specific binding pair, following deposition, the substrate-specific binding partner complex is reacted with the second member of the binding pair which is coupled to a reporter. Alternately, the substrate-specific binding partner complex can be pre-reacted with the detectably labeled other member of the specific binding pair prior to deposition.

The term deposition means directed binding of an activated conjugate to the receptor which results from the formation of a specific binding pair interaction as described below.

The term receptor means a site which will bind to the activated conjugate through the formation of a specific binding pair interaction as described below.

The term activated conjugate means that the conjugate has been primed by the ADEAS to bind with the receptor.

One of the unique features of this invention is the analyte dependent enzyme activation system which catalyzes deposition of conjugate by converting the substrate portion of the conjugate to an activated form which is deposited wherever a specific receptor for the activated conjugate is immobilized. The ADEAS does not utilize enzyme cascade reactions or enzyme cycling to effect amplification. Rather, it uses either a single enzyme or combination of enzymes to activate the conjugate. Deposition of conjugate occurs only if the analyte and analyte dependent enzyme activation system, which can be the same if the analyte is an enzyme, for example in the detection of an enzyme such as alkaline phosphatase, or different, have been reacted and a receptor, as described below, is immobilized to bind the activated conjugate. Thus, the ADEAS, conjugate, and receptor are chosen to form an operational trio.

The following is one embodiment of a single enzyme ADEAS system applied to a forward sandwich immunoassay format: the test sample containing the analyte is reacted with an immobilized capture reagent, such as an antibody; excess reagents are washed off; the immobilized capture antibody-analyte complex is reacted with an ADEAS, such as a second antibody specific for the analyte which has been coupled to an enzyme, e.g. horseradish peroxidase (HRP), alkaline phosphatase (AP), etc. The ADEAS will bind only if the analyte has been bound by the capture reagent. Otherwise the reagents will be washed off. Coupling of the enzyme to a specific binding partner does not affect the enzyme's ability to react with the substrate portion of the conjugate. When conjugate such as biotin-tyramine is added to the immobilized capture antibody-analyte-second antibody-enzyme complex, the enzyme reacts with the substrate portion of the conjugate, in this case, with the tyramine portion of the conjugate, converting it to an active form which will bind to an immobilized receptor which is either endogenous or exogenous to the assay system. The amount of conjugate deposited will be a function of immobilized ADEAS. Deposited conjugate such as biotin-tyramine can then be detected by reacting with streptavidin-HRP and orthophenylenediamine. If the conjugate is fluorescein-tyramine then the deposited conjugate can be detected directly, or following reaction with a labeled anti-fluorescein antibody.

Figure 3:
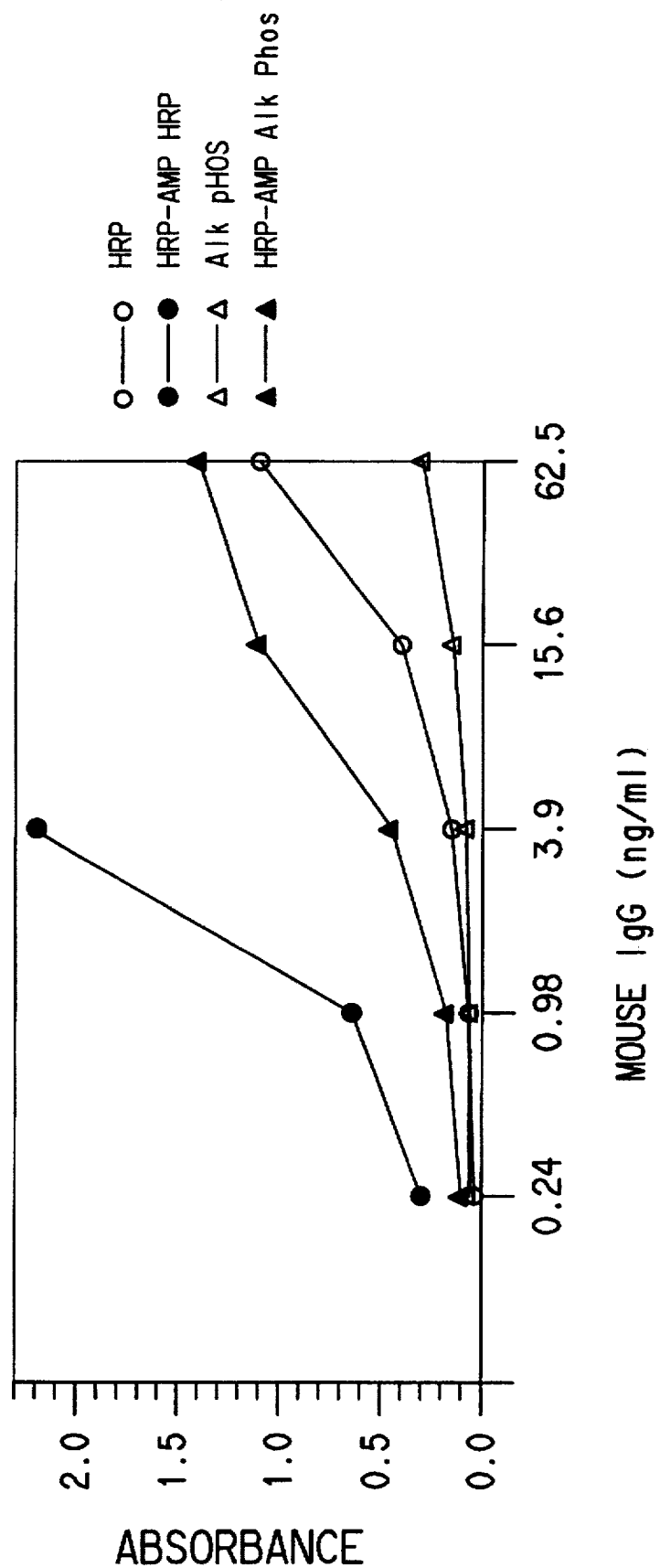
FIG. 3 is a graph of a mouse IgG assay run using an HRP ADEAS to catalyze deposition of biotin-tyramine which was detected with streptavidin-HRP (HRP-Amp HRP) or with streptavidin-AP (HRP-Amp AP). The assay was also run using only HRP labeled detector antibody or AP labeled detector antibody.

Thus, the ADEAS is used to catalyze the deposition of detectably labeled substrate (the conjugate) to generate additional signal. The ADEAS is detected directly as part of the overall signal when the enzyme component of the ADEAS is the same as the enzyme used as the reporter. FIG. 3 illustrates this situation as well as the situation where an ADEAS enzyme component and reporter enzyme are different and thus, the ADEAS enzyme component is not detected directly as part of the overall signal.

A multi-enzyme ADEAS immunoassay format would involve a similar approach. For example, the ADEAS can be an antibody coupled to an enzyme such as neuraminidase which is reacted with immobilized capture antibody and analyte to form an immobilized capture antibody-analyte-second antibody-neuraminidase complex. A second enzyme such as β-galactosidase is added together with the conjugate. The conjugate can be a detectably labeled moiety containing a sialyl-galactosyl glycoside. Neuraminidase releases the terminal sialic acid residue which then enables β-galactosidase to remove the galactose group. Without the release of the terminal sialic acid residue, the β-galactosidase cannot remove the galactose group. Once deglycosylation is complete, the activated conjugate deposits wherever receptors for the activated conjugate are immobilized.

The instant invention is surprising and unexpected because amplification of reporter signal is obtained via deposited activated conjugate without using cascade mechanisms or enzyme cycling. The ADEAS reacts with the conjugate to form an activated conjugate which will bind with immobilized receptor specific for the activated conjugate. The amounts of receptor and activated conjugate are in excess of the amount of ADEAS immobilized.

The choice of an ADEAS is governed by the ability of the enzyme or enzymes to convert a conjugate to an activated form which will bind to an immobilized receptor whether endogenous or exogenous. Accordingly, a detailed knowledge of catalytic properties of each specific enzyme is needed in order to properly design the substrate and receptor. Other important factors include availability of the enzyme or enzymes, relative ease or difficulty of coupling it to the member of a specific binding pair, stability of the enzyme or enzymes as well as the stability of the conjugate and the receptor. In some cases, an ADEAS can be purchased, depending on the assay format.

Enzymes suitable for use in an ADEAS include hydrolases, lyases, oxidoreductases, transferases isomerases and ligases. There can be mentioned peroxidases, oxidases, phosphatases, esterases and glycosidases. Specific examples include alkaline phosphatase, lipases, beta-galactosidase and horseradish peroxidase.

Members of specific binding pairs suitable for use in practicing the invention can be of the immune or non-immune type. Immune specific binding pairs are exemplified by antigen/antibody systems-or hapten/anti-hapten systems. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')$_2$ fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

Suitable supports used in assays include synthetic polymer supports, such as polystyrene, polypropylene, substituted polystyrene, e.g., aminated or carboxylated polystyrene; polyacrylamides; polyamides; polyvinylchloride, etc.; glass beads; agarose; nitrocellulose; nylon; polyvinylidenedifluoride; surface-modified nylon, etc.

Another important component of the invention is the conjugate, i.e., a detectably labeled substrate which must be specific for the ADEAS. As was stated above, when the conjugate reacts with the ADEAS, the enzyme or enzymes catalyze formation of an activated conjugate which binds wherever a receptor is immobilized whether exogenous or endogenous. The activated conjugate binds to the receptor via a specific binding pair interaction as described above. An immobilized exogenous receptor means a receptor which does not originate within the assay. It must be immobilized on the surface of a support prior to adding the conjugate to the reaction mixture. An endogenous receptor means a receptor which originates within the assay and does not require immobilization prior to adding the conjugate because the receptor is immobilized within the assay system.

For example, when an HRP ADEAS (HRP coupled to a member of a specific binding pair) is reacted with conjugate containing a phenolic substrate, an activated phenolic substrate is produced. It is believed that the activated phenolic substrate binds to electron rich moieties such as tyrosine and tryptophan present in the proteins on the solid support. However, if a different conjugate is used, such as a labeled MBTH which is discussed below, a receptor, such as an analog of DMAB, must be immobilized prior to addition of conjugate.

Another embodiment involves reacting a conjugate which becomes phosphorylated by an ADEAS. The activated (phosphorylated) conjugate can then react with an antibody specific for the activated conjugate.

In still another variation, an ADEAS can be reacted with a conjugate consisting of a component which when activated will bind to a receptor and which is coupled to a component having a thiol reactive group such as a maleimide. The deposited maleimide moiety can then be detected by reacting with a sulfhydryl-containing reporter which can be endogenous to the reporter, e.g., beta-galactosidase, or the sulfhydryl groups can be added to reporters such as HRP or AP using thiolating reagents such as N-succinimidylisacetylthioacetate (SATA), S-acetylmercaptosuccinic anhydride (SAMSA), or succinimidyl-3-(acetylthio)-propionate (SATP).

Alternatively, the substrate can be coupled to a protected sulfhydryl containing group and this can be used as the conjugate. After binding to the receptor, this can be deprotected using conventional techniques known to those skilled in the art. Detection can be effected using a reporter having a thiol reactive group such as maleimide-HRP or iodoacetyl-HRP.

Another alternative is to use a conjugate wherein the substrate has two components as described above, a detectably labeled first component which will bind to the receptor after the second component has been activated or removed by the ADEAS.

Other small organic molecule/receptor combinations which are suitable to practice the invention include haptens/antibodies, sugars and oligosaccharides/lectins, biotin and avidin/streptavidin.

As is shown in Table 1, a number of receptors are available. The choice of a receptor will depend upon the conjugate selected.

The optimal concentration of conjugate is determined according to the procedure explained in Example 1. Optimal concentrations will vary depending upon enzyme used in the ADEAS and substrate selected to produce conjugate.

Conjugate can be synthesized using conventional coupling and labeling techniques. Substrate choice will depend upon the ADEAS selected. To reiterate, detailed knowledge is required of the catalytic properties of each specific enzyme in order to properly design a useful synthetic substrate and, if necessary, a receptor.

A wide variety of reporters are available for coupling to the substrate to produce the conjugate or to couple to a member of a specific binding pair. As was discussed above reporter should introduce a different moiety to the substrate. Reporters can be a radioactive isotope, such as, $^{125}I$, enzymes, fluorogenic, chemiluminescent, or electrochemical materials. Internally labeled reporters (e.g., tritium or other such radionuclides) which do not introduce a different moiety to the substrate are not contemplated for practicing the invention.

Examples of reporter enzymes which can be used to practice the invention include hydrolases, lyases, oxidoreductases, transferases, isomerases and ligases. Some preferred examples are phosphatases, esterases, glycosidases and peroxidases. Specific examples include alkaline phosphatase, lipases, beta-galactosidase and horseradish peroxidase. As was noted above, if an enzyme is used as a reporter, it can be the same as or different from the enzyme or enzymes used in the ADEAS. The instant invention can be used to catalyze deposition of a radioisotopically labeled conjugate or an enzyme-labeled conjugate, etc.

Another embodiment of the forward sandwich immunoassay described above would involve reacting a capture-antibody-analyte-second antibody complex with an ADEAS consisting of an anti-antibody coupled to an enzyme such as HRP or AP. The anti-antibody would bind an epitope on the second antibody.

This invention is not limited to sandwich immunoassays. It is applicable to a wide variety of assay formats, for example, nucleic acid hybridization assays for both RNA and DNA.

To further illustrate the invention, examples of single and multi-enzyme ADEAS, conjugates, receptors, and receptor types are presented in Table 1 below.

TABLE 1

| ADEAS | | CONJUGATE[2] | RECEPTOR | |
|---|---|---|---|---|
| Class | Enzyme | Substrate | Class | Type |
| Single Enzyme | HRP[1] | Substituted phenols, e.g., tyramine | Endogenous | Phenols; electron rich moieties |
| Single Enzyme | HRP[1] | MBTH | Exogenous | DMAB |
| Single Enzyme | β-Galactosidase | β-Galactopyranosyl-glycoside, e.g., of fluorescein, coumarin, | Exogenous | Antibody to deglycosylated moiety, e.g., |

TABLE 1-continued

| ADEAS | | CONJUGATE[2] | RECEPTOR | |
|---|---|---|---|---|
| Class | Enzyme | Substrate | Class | Type |
| | | etc. | | anti-fluorescein; anti-coumarin |
| Single Enzyme | AP | NADP | Exogenous | NAD binding proteins |
| Single Enzyme | AP | Substituted phosphates, e.g., nitrophenyl phosphate | Exogenous | Antibody to dephosphorylated product, e.g., anti-nitro-phenol |
| Single Enzyme | AP | Phosphorylated biotin | Exogenous | Avidin; streptavidin |
| Multi-Enzyme | AP and HRP[1] | Phosphorylated substituted phenols, e.g., tyrosine phosphate | Endogenous | Phenols; electron rich moieties |
| Multi-Enzyme | Neuraminidase and β-galactosidase | Sialyl-β-galactopyranosyl-glycoside of coumarin | Exogenous | Antibody to deglycosylated moiety, e.g., anti-coumarin |

[1]HRP requires the presence of $H_2O_2$.
[2]Label can be a reporter or member of a specific binding pair.

In the AP/HRP multi-enzyme ADEAS described above, the conjugate must be dephosphorylated before it will react with HRP; and in the β-gal/neuraminidase multi-enzyme ADEAS, the conjugate must be desialylated before it will react with β-gal.

It should be clear to those skilled in the art that a large number of variations are possible and all these variations fall within the scope of the invention.

The following examples are intended to illustrate the invention. Unless otherwise indicated, 100 μl of all reagents were used for the EIA strip assays. The one exception was that 200 μl of blocking buffer was used.

EXAMPLE 1

Preparation of Conjugates and Optimization of Conjugate Concentration

Para-hydroxyphenylpropionyl biocytin (HPPB) was prepared by mixing a solution of p-hydroxyphenylpropionic acid-N-hydroxysuccinimide ester. (50 mg [0.2 mMol]/2 ml dimethyl sulfoxide) with biocytin (70.75 mg [0.2 mMol]/2 ml 0.1M $NaHCO_3$) overnight at room temperature (RT). Biotin-tyramine (BT) was prepared by mixing a solution of tyramine (40 mg [0.3 mMol]/1 ml dimethyl sulfoxide) with biotin-N-hydroxysuccinimide ester (100 mg [0.3 mMol]/1 ml dimethyl sulfoxide) overnight at RT. The solutions of HPPB and BT were used as is. The calculated concentrations were 26 mg/ml for HPPB and 55 mg/ml for BT.

Polystyrene EIA strips (NUNC) were coated with polyclonal anti-Herpes Simplex Virus (HSV) antibody (Dako, Carpenteria, Calif.) in 0.1M carbonate buffer pH 9.6 overnight at 4° C., and then blocked with 2% bovine serum albumin (BSA) in carbonate buffer and then washed with 10 mM phosphate buffered saline, 0.05% Tween 20, pH 7.4 (PBST). A dilution of HSV antigen in 1% BSA, 10 mM phosphate buffered saline, 0.05% Tween 20 pH 7.4 (BSA-PBST), or buffer without antigen, was incubated for 1 hour at 37° C. The dilution was sufficient to obtain the optical densities in the range reported in Table 1. It was washed with PBST. The analyte dependent enzyme activation system consisted of HRP coupled to anti-HSV (HRP ADEAS) which was purchased from Dako. The HRP ADEAS was added and incubated for 30 min. at RT and was washed with PBST. Various concentrations of HPPB or BT as set forth in Table 1 were added in 50 mM tris-HCl, 0.01% $H_2O_2$, pH 8.0, for 15 min. at RT. After washing with PBST, streptavidin-HRP was added and incubated for 15 min. at RT to react with deposited biotins. The plate was then washed with PBST. An HRP substrate, o-phenylenediamine (OPD), was added, incubated for 30 min. at RT, and stopped with 4N $H_2SO_4$. Optical densities at 490 nm were recorded on a microtiter plate reader.

Results

Results are presented in Table 2. Column 1 presents the various concentrations in μl/ml of HPPB or BT. Columns 2 and 3 present the optical densities recorded as a function of HPPB concentration. Columns 4 and 5 present the results obtained using BT.

HPPB and BT were converted to activated forms by HRP ADEAS. Catalyzed reporter deposition was achieved without immobilizing a receptor.

In choosing the optimal concentration, one must look at both the magnitude of signal amplification as well as the signal to noise ratio. With this in mind, the optimal concentration of HPPB was 20 μl/ml (approximately 0.5 mg/ml), and that of BT, was about 0.3 μl/ml (approximately 16 μg/ml).

TABLE 2

| | Absorbance 490 nm | | | |
|---|---|---|---|---|
| Conc. HPPB | HPPB CONJUGATE | | BT CONJUGATE | |
| or BT (μl/ml) | HSV | Buffer (w/o Ag)* | HSV | Buffer (w/o Ag) |
| 0 | 0.079 | 0.031 | 0.079 | 0.031 |
| 20 | 1.155 | 0.181 | 0.700 | 0.165 |
| 10 | 0.904 | 0.140 | — | — |
| 5 | 0.499 | 0.120 | 2.060 | 0.430 |
| 2.5 | 0.177 | 0.063 | — | — |
| 1.25 | 0.113 | 0.062 | 2.230 | 0.502 |
| 0.625 | 0.103 | 0.048 | — | — |
| 0.313 | — | — | 1.880 | 0.169 |
| 0.078 | — | — | 0.263 | 0.051 |
| 0.020 | — | — | 0.090 | 0.040 |

*w/o Ag = without antigen

EXAMPLE 2

Amplification of Detector Signal in HSV Assay Using Catalyzed Reporter Deposition Anti-HSV coated EIA strips were prepared as described in Example 1. A 1:100 dilution of HSV antigen was prepared and serially four-fold diluted. These dilutions of HSV were incubated for 2 hours at 37° C. with the anti-HSV coated EIA strips. Excess reagent was washed off with PBST. The ADEAS was the same as that described in Example 1 above. It was added to the anti-HSV coated EIA strips containing the anti-HSV-HSV complex and incubated for 30 min. at RT and then washed with PBST. 20 μl/ml of HPPB conjugate as determined in Example 1 was added in 50 mM tris-HCl, 0.01% $H_2O_2$, pH 8.0, and was incubated for 15 min. at RT and then washed with PBST. Deposited biotins were reacted with streptavidin-HRP (SA-HRP) for 15 min. at RT followed by washing with PBST. The substrate, OPD, was added and incubated 30 min. at RT, stopped with 4N $H_2SO_4$, and the absorbance at 490 nm was recorded on a microtiter plate reader.

Non-amplified assays were run in which (a) no HPPB and no SA-HRP were used; (b) HPPB was used without SA-HRP; (c) SA-HRP was used without HPPB.

Results

The results shown in FIG. 1 demonstrate that (a) catalyzed deposition of reporter was obtained and (b) both the conjugate and SA-HRP were needed for detection because the conjugate contained an unlabeled member of a specific binding pair.

Results for the non-amplified assay (no HPPB, no SA-HRP) were plotted. The results for the other assays were not plotted because the additional plots would overlap with the non-amplified results already plotted.

EXAMPLE 3

Figure 2:
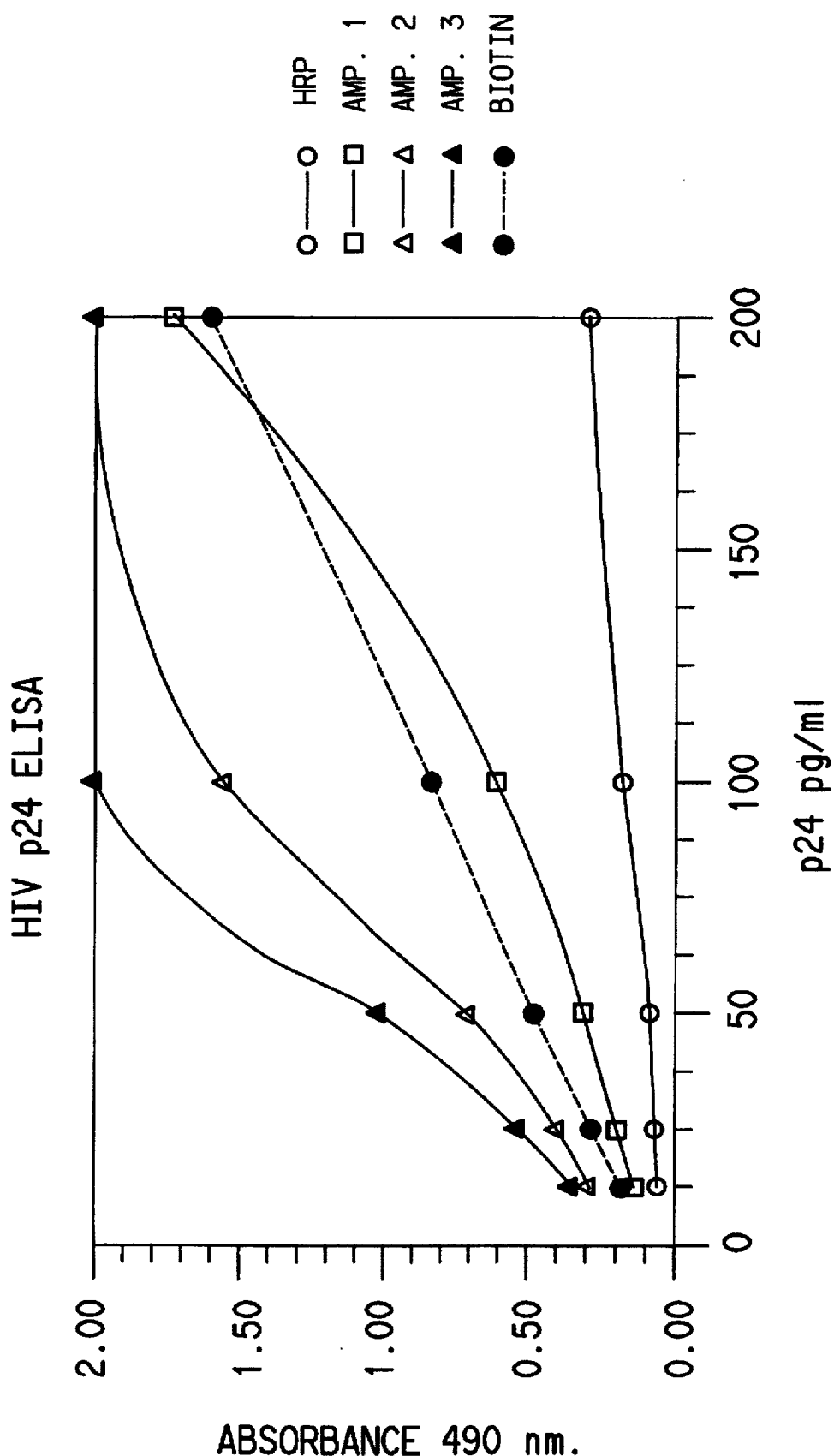
FIG. 2 is a graph comparing results of an HIV p24 core antigen assay using conjugate concentrations of 0.2, 0.4, and 0.8 µl/ml (Amp 1, 2, and 3, respectively). "HRP" represents a non-amplified assay wherein the detector antibody was directly labeled with HRP. "Biotin" indicates another non-amplified assay wherein the detector antibody was conjugated to biotin and detected with HRP labeled streptavidin.

Amplification of Detector Signal in HIV p24 Assay Using Catalyzed Reporter Deposition: Effect of Conjugate Concentration Polystyrene EIA strips (NUNC) were coated with rabbit anti-HIV p24 antibodies in 0.1M carbonate buffer, pH 9.6, overnight at 4° C., and then blocked with 2% BSA in carbonate buffer followed by washing with PBST. HIV antigen was incubated for 2 hours at 37° C. (concentrations are indicated in FIG. 2). The plate was then washed with PBST. A rabbit anti-HIV p24-HRP analyte dependent enzyme activation system was then incubated for 2 hours at 37° C., and washed with PBST. Various concentrations of BT conjugate, (0.2, 0.4, and 0.8 μl/ml) in 0.1M borate buffer, 0.01% $H_2O_2$, pH 8.5, were incubated for 15 min. at RT followed by washing with PBST. Then streptavidin-HRP was incubated for 15 min. at RT.

As a comparison, a biotinylated anti-HIV p24 antibody was used, and detected with streptavidin-HRP. OPD was added and incubated for 30 minutes, stopped with 4N $H_2SO_4$, and optical densities at 490 nm were recorded on a microtiter plate reader.

Results

The results are shown in FIG. 2 where Amp 1, Amp 2, and Amp 3 refer to BT at concentrations of 0.2, 0.4, and 0.8 μl/ml respectively. Different levels of amplification were achieved using catalyzed reporter deposition depending on the concentration of conjugate.

FIG. 2 also presents results for a non-amplified assay using a biotinylated antibody/SA-HRP detection system (Biotin) and a non-amplified assay wherein anti-HIV p24 detector was directly labeled with HRP (HRP). The results obtained using the anti-HIV p24-HRP detector were inferior compared to the significant increase in detector signal obtained using catalyzed reporter deposition.

Depending upon the concentration of conjugate, signals as good, and greater, as those obtained with the biotinylated antibody were obtained using the catalyzed reporter deposition method of the instant invention. Best results were obtained using conjugate concentration near the optimal amount as was determined in Example 1.

EXAMPLE 4

Preparation and Characterization of Biotin Tyramine

Synthesis of biotin-tyramine: a solution of biotin-N-hydroxysuccinimide, 170 mg (0.5 mMoles), and tyramine (recrystallized from water), 68.5 mg (0.5 mMoles), in 25 ml dimethylformamide was treated with 10 ml of 1M triethylammonium bicarbonate, pH 7.5, and then heated at 50° C. for 3 hours.

Isolation: the solution was concentrated to dryness on a rotary evaporator, and the residue was recrystallized from water, with a yield of 72%.

Characterization: the melting point was determined to be 192°–193° C.

EXAMPLE 5

Amplification of Detector Signal in a Mouse IgG Assay Using Catalyzed Reporter Deposition Polystyrene EIA strips (NUNC) were coated with goat anti-mouse IgG (Fc fragment specific) antibody (ICN) in 0.1M carbonate buffer pH 9.6, overnight at RT. They were then blocked with 2% BSA in carbonate buffer and washed with PBST. Dilutions of mouse IgG in BSA-PBST were incubated in the wells for 1 hour at 37° C. followed by washing with PBST. Concentrations are set forth in FIG. 3. Goat anti-mouse IgG-HRP (HRP ADEAS) and goat anti-mouse IgG-Alkaline Phosphatase (AP ADEAS) (Boehringer Mannheim) were diluted as recommended by the manufacturer and incubated for 1 hour at 37° C. Assays were run with and without catalyzed reporter deposition. The AP ADEAS was not used to catalyze reporter deposition in this experiment.

For catalyzed reporter deposition using the HRP ADEAS, a 1 mg/ml stock solution of biotin tyramine (as described in Example 4) in dimethyl sulfoxide was prepared, and then added to a 0.1M borate buffer, pH 8.5, 0.01% $H_2O_2$, at 10 μl/ml (10 μg/ml biotin tyramine) and incubated for 15 min. at RT. The plate was then washed with PBST. Streptavidin-HRP (for HRP-Amp HRP), or streptavidin-Alkaline Phosphatase (for HRP-Amp Alk Phos) were incubated for 15 min. at RT and the plate was washed with PBST. Spectrophotometric detection was achieved after the addition of OPD (for HRP), or p-nitrophenyl phosphate (for AP) for 15 min. at RT. Reactions were stopped by the addition of 4N $H_2SO_4$ (HRP/OPD), or 1N NaOH (Alk Phos/pNPP). Optical densities, at 490 nm for HRP/OPD and 405 nm for Alk Phos/pNPP, were recorded on a microtiter plate reader.

Results

The results are shown in FIG. 3. As is apparent, one can achieve signal amplification with a concomitant lower detection limit by allowing the HRP ADEAS to catalyze deposition of an activated BT conjugate followed by detection with streptavidin coupled to HRP or AP. This example shows that if the reporter is an enzyme, it can be the same as, or different from, the enzyme used in the ADEAS.

EXAMPLE 6

Amplification of Detector Signal in an Assay For HIV p24 Which Utilizes a Biotinylated Detector Antibody/Streptavidin-HRP Detection System The Du Pont HIV p24 Antigen ELISA (catalog number NEK 060) was modified for catalyzed reporter deposition as follows: SA-HRP was used at ¼ the concentration indicated in the directions. This was followed by a 15 min. RT incubation with biotin-tyramine, 10 µg/ml, in 0.1M borate, 0.01% $H_2O_2$ pH 8.5 buffer (as in Example 5). Following washing with PBST, SA-HRP at $\frac{1}{16}$ the concentration was incubated for 15 min. at RT. Finally, OPD was added as per kit directions. Except for extending the standard concentrations down to 0.39 pg/ml, no other changes were made.

Results

Figure 4A:
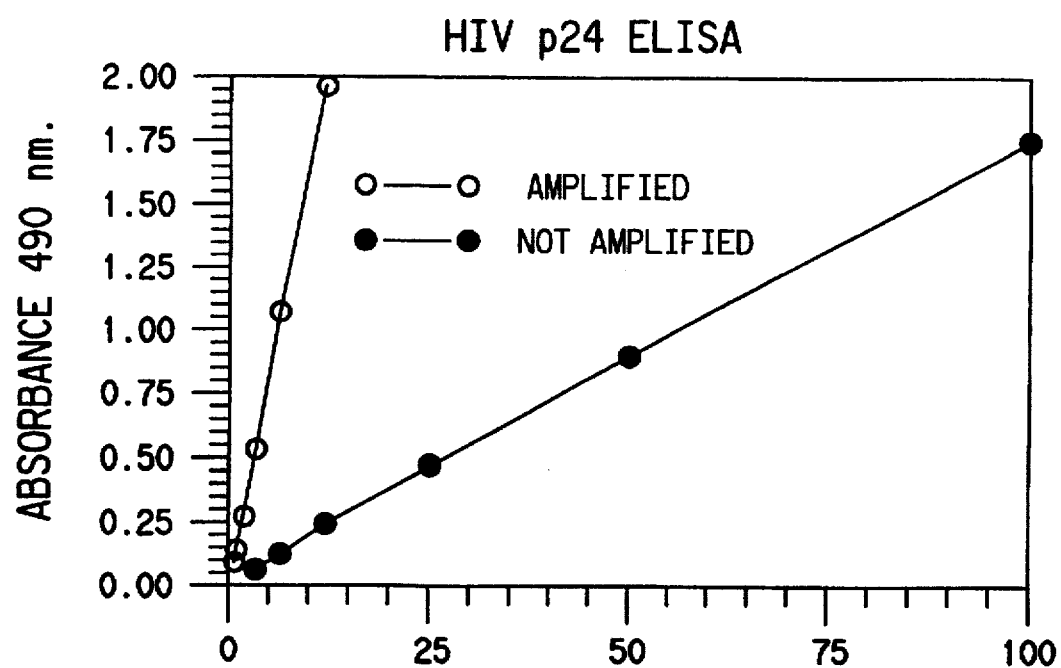
FIG. 4 presents two graphs comparing results obtained from a Du Pont HIV p24 antigen ELISA run with and without using catalyzed reporter deposition to amplify reporter signal.
Figure 4B:
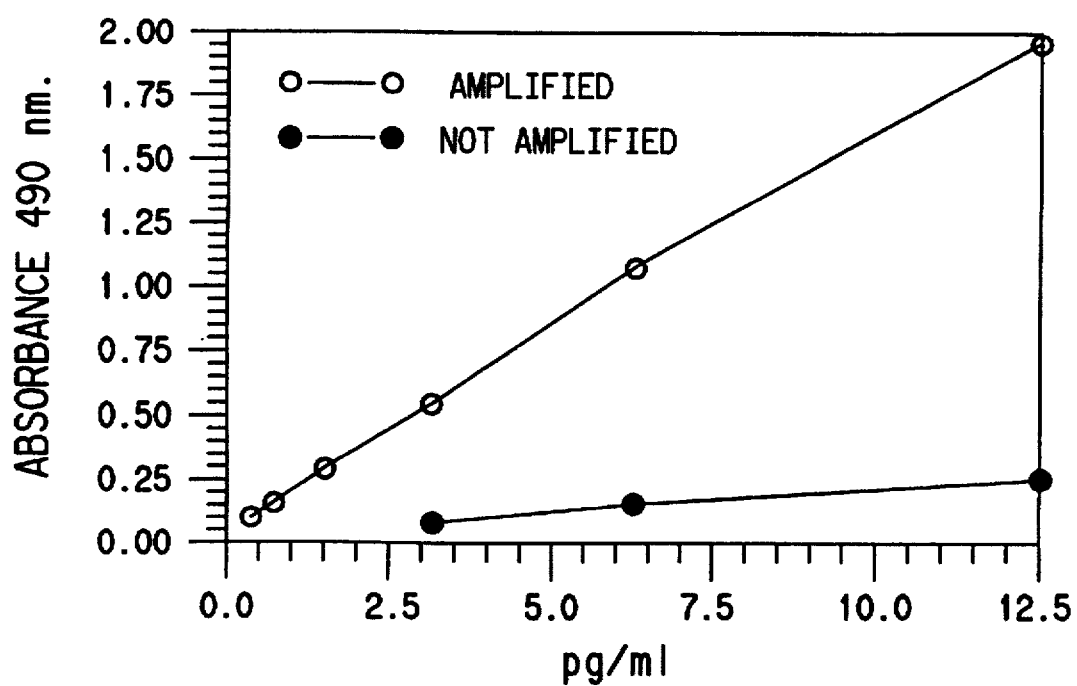

The results are shown in FIG. 4. This experiment demonstrated that one can amplify the signal generated by a biotinylated antibody/SA-HRP system using catalyzed reporter deposition. Because the concentration of SA-HRP for both incubations was much less than that for the non-amplified assay, it was clear that the increased signal was attributable to reporter deposition and not to a double SA-HRP incubation.

EXAMPLE 7

Reporter Deposition on Membranes

Nitrocellulose (Schleicher & Schuell, BA 85) was spotted with HSV antigen, and then blocked with 1% BSA, 1% non-fat dry milk, in PBS buffer, overnight. The membranes were incubated for 1 hour at RT with the analyte dependent enzyme activation system described in Example 1 above. The membranes were then incubated with biotin tyramine (from Example 1) at 2 µl/10 ml 50 mM tris-HCl, 0.01% $H_2O_2$, pH 8.0 buffer for 15 min. at RT, which was followed by incubation with streptavidin-alkaline phosphatase for 15 min. at RT. Controls were run where biotin tyramine was incubated without streptavidin-alkaline phosphatase, and streptavidin-alkaline phosphatase was incubated without biotin-tyramine. Visualization of deposited alkaline phosphatase was facilitated by the addition of BCIP/NBT (Kirkegaard & Perry). BCIP is 5-bromo-4-chloro-indoxyl phosphate and NBT is 2,2'-di-(p-nitrophenyl)-5,5'-diphenyl-3,3'-(3,3'-dimethoxy-4,4'-diphenylene)-ditetrazolium chloride. Visualization of the bound anti-HSV-HRP conjugate was facilitated by the addition of diaminobenzidine (DAB).

Results

Addition of DAB produced observable brown spots where HSV antigen was spotted on the nitrocellulose membrane. Addition of BCIP/NBT produced observable blue spots where HSV antigen was spotted when biotin tyramine and streptavidin-alkaline phosphatase were incubated with the membrane. This showed that alkaline phosphatase was deposited due to HRP activation of the biotin tyramine conjugate, followed by streptavidin-alkaline phosphatase detection.

EXAMPLE 8

Deposition of Beta-Galactosidase by Horseradish Peroxidase, and Detection by Fluorescence Polystyrene EIA strips (NUNC) were coated with goat anti-mouse IgG (Fc fragment specific) antibody (ICN) in 0.1M carbonate buffer, pH 9.6, overnight at RT. They were then blocked with 2% BSA in carbonate buffer and washed with PBST. Concentrations of mouse IgG in BSA-PBST, as set forth in FIG. 5, were incubated for 1 hour at 37° C. followed by washing with PBST. Goat anti-mouse IgG-HRP (ADEAS) purchased from Boehringer Mannheim was diluted as recommended by the manufacturer and incubated for 1 hour at 37° C. The plate was then washed with PBST. A 1 mg/ml stock solution of BT conjugate (as described in Example 4) in dimethyl sulfoxide was prepared, and then added to a 0.1M borate, 0.01% $H_2O_2$, pH 8.5 buffer at 10 µl/ml (10 µg/ml biotin tyramine). The mixture was added to the plate and incubated for 15 min. at RT, and then washed with PBST. Streptavidin-beta galactosidase (Bethesda Research Labs) was added and incubated for 15 min. at RT. The assay was also run without catalyzed reporter deposition, i.e., without adding BT. Colorimetric detection of the non-amplified assay was achieved after incubation with OPD (for HRP), for 15 min. at RT. Fluorescent detection of the amplified assay was achieved after the addition of 4-methylumbelliferyl beta-D-galactoside (MUG) (for HRP-beta Gal). Optical densities at 490 nm were recorded for HRP/OPD on a microtiter plate reader. Fluorescence for HRP-beta Gal/MUG was recorded on a fluorescence microtiter plate reader (Dynatech Laboratories).

Results

Figure 5:
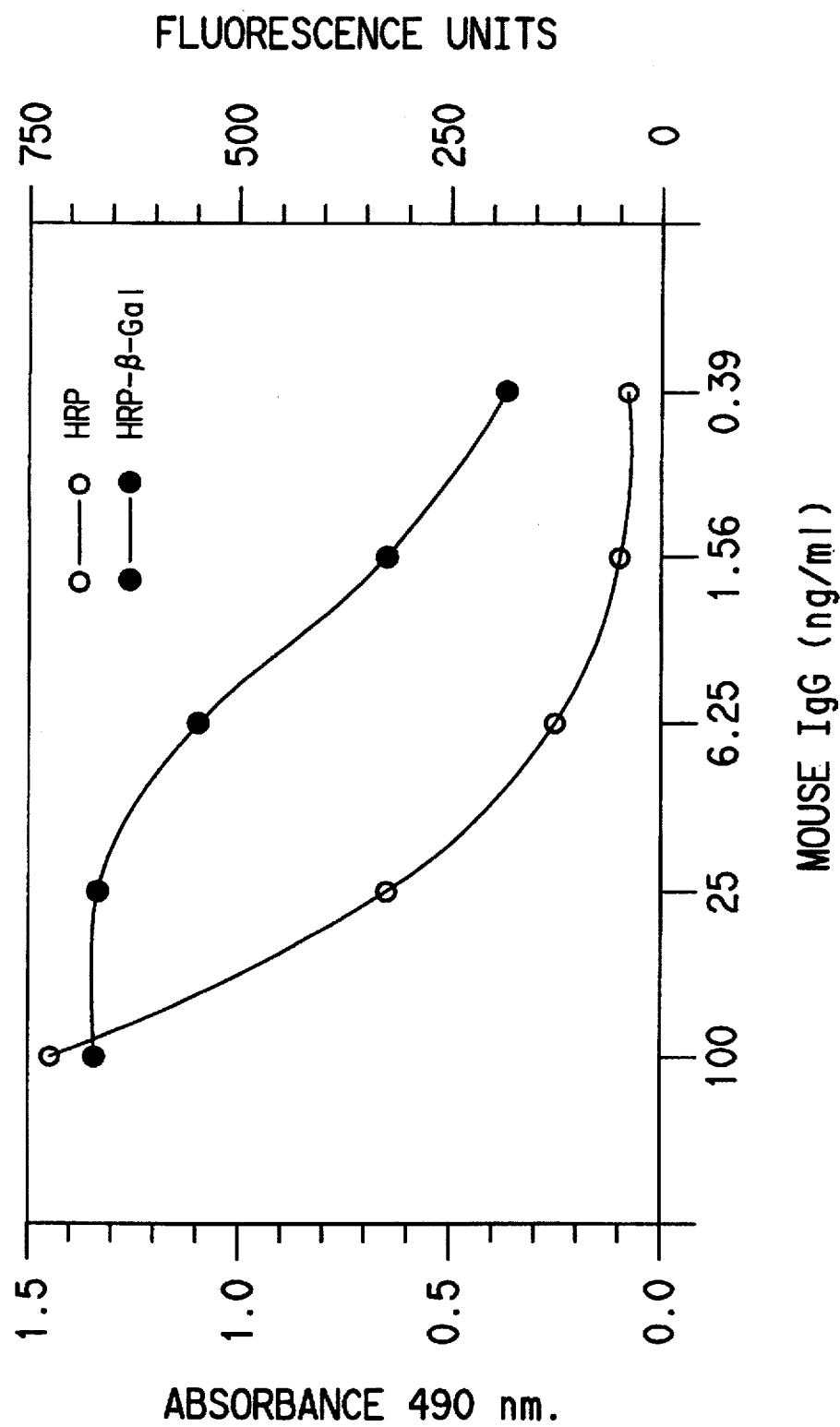
FIG. 5 is a graph comparing results of a mouse IgG assay without catalyzed reporter deposition (HRP) and with catalyzed reporter deposition (HRP-β-Gal).

The results are shown in FIG. 5. The fluorescent signal was due to the quantitative deposition of biotin tyramine by the HRP ADEAS followed by incubation with streptavidin beta-galactosidase.

EXAMPLE 9

Amplification of a Membrane Assay

Fluorescein-tyramine (FT) was prepared as follows: Solutions of 46.6 mg of 5-(and 6)-carboxyfluorescein succinimidyl ester in 0.3 ml dimethyl sulfoxide and 14.6 mg tyramine in 0.3 ml dimethyl sulfoxide were prepared. Conjugation was achieved by mixing 0.25 ml of each solution overnight at RT. The solution was used as is.

Three nitrocellulose (Schleicher & Schuell, BA 83) strips were spotted with 1 µl of mouse IgG at 10 µg/ml, and serial two fold dilutons in PBS. The membranes were blocked with 5% non-fat dry milk in PBST for 30 min, and then washed three times in PBST. A goat anti-mouse IgG-HRP conjugate (Boehringer Mannehim) diluted $\frac{1}{2000}$ in 1% BSA-PBST was incubated for 30 min. at RT, and the membranes were washed three times with PBST. The third membrane was incubated with FT at 20 µg/ml in 0.1M borate, 0.01% $H_2O_2$, pH 8.5 buffer for 15 min. at RT, and washed three times in PBST. Then, the second and third membranes were incubated with an anti-fluorescein antibody. (Chemicon) which was conjugated to HRP (by the SMCC method of Ishikawa, E., et al., J. Immunoassay, 4, 209–327, 1983) diluted in 1% BSA-PBST for 15 min at RT, and washed three times in PBST. Visualization of all three strips was facilitated by the addition of diaminobenzidine for 5 min.

Results

Three spots could be seen on the first two strips indicating a detection limit of 2.5 µg/ml, and that the anti-fluorescein-HRP conjugate did not contribute to additional signal. Six spots could been seen on the third strip indicating a detection limit of 313 ng/ml. The use of the catalyzed reporter deposition amplification method of the invention improved the detection limit of the assay eight fold over that of the non-amplified assay.

EXAMPLE 10

Preparation of 7-(β-Galactosyl)-4-Methylcoumarin-3-Acetamidobiocytin a) 7-Hydroxy-4-methylcoumarin-3-acetic acid, ethyl ester (2)

7-Hydroxy-4-methylcoumarin-3-acetic acid (1) (1 gm, 4.3 mmol) was suspended in anhydrous ethanol (15 mL), concentrated sulfuric acid (1.5 mL) was added and the mixture was heated at reflux for 1 hour. The reaction mixture was cooled to room temperature, diluted with ethyl acetate (100 mL), washed with 5% NaHCO$_3$ (5×50 mL), water (2×50 mL), saturated NaCl (2×50 mL) dried with sodium sulfate, filtered and the filtrate was evaporated under reduced pressure to give 1.04 gm (4.0 mmol, 92% yield of 2 as a white solid.

$^1$H NMR (CDCl$_3$/DMSO-d$_6$): 1.19 (3H, t), 2.29 (3H, s), 3.57 (2H, s), 4.06 (2H, q), 6.65 (1H, d), 6.73 (1H, dd), 7.44 (1H, d).

TLC: Silica gel, 3% methanol, 1% acetic acid, methylene chloride, R$_f$=0.25.

b) 7-(Tetraacetyl-β-galactosyl)-4-methylcoumarin-3-acetic acid, ethyl ester (3)

To a stirred solution of 7-hydroxy-4-methylcoumarin-3-acetic acid, ethyl ester (2) (1.04 gm, 4.0 mmol), bromo-tetraacetyl-β-galactoside (1.4 gm, 3.41 mmol) in acetone (20 mL) was added 1N NaOH (3.6 mL) dropwise. The reaction was stirred at room temperature overnight and TLC (silica gel, 3% methanol, 1% acetic acid, methylene chloride) showed about a 50% conversion of starting material to a faster moving spot so an additional 0.36 mL of NaOH and 200 mg (0.49 mmol) of bromo-tetraacetyl-β-galactoside were added and stirring continued for 1 hour. TLC showed no change so the reaction mixture was diluted with ethyl acetate (100 mL) and washed with water (3×50 mL), saturated sodium chloride (2×30 mL), dried with sodium sulfate, filtered and the filtrate was evaporated under reduced pressure to give a yellow oil which was purified by silica gel chromatography eluting with 2% methanol in methylene chloride. Fractions containing the desired product by TLC were pooled and evaporated to give 1.51 gm of a white foam which was crystallized from 50% ethanol to give 879 mg (1.51 mmol), 38%) of 3 as white needles: m.p. 195°–197° C.

$^1$H NMR (CDCl$_3$): 1.25 (3H, t), 2.0 (3H, s), 2.07 (3H, s), 2.09 (3H, s), 2.17 (3H, s), 2.37 (3H, s), 3.7 (2H, s), 4.1 (5H, m), 5.1 (2H, m), 5.5(2H, m), 6.9 (2H, m), 7.5 (1H,m).

TLC: Silica gel, 3% methanol, 1% acetic acid, methylene chloride, R$_f$=0.35.

c) 7-(β-galactosyl)-4-methylcoumarin-3-acetic acid (4)

To a stirred solution of 7-(tetraacetyl-β-galactosyl)-4-methylcoumarin-3-acetic acid, ethyl ester (3) (422 mg, 0.712 mmol) in methanol was added 6.8M KOH (5 mL) and the solution was stirred overnight at room temperature. The solution was neutralized by the addition of 1N HCl and evaporated to dryness under reduced pressure. The residue was dissolved in water (10 mL) and desalted using C$_{18}$ Sep Pack Cartridges in 10×1 mL portions. The C$_{18}$ Sep Pack Cartridge (Waters Part No. 65910) was washed with methanol (3 mL) and water (3 mL) before the sample was applied in 1 mL. The cartridge was then washed with water (3 mL) to remove any salt followed by metahnol (3 mL) which eluted the desired product as determined by TLC (silica gel, acetone:20 mM NaOAc 9:1). The methanol washes were pooled and evaporated under reduced pressure and the while solid obtained was recrystallized from ethanol/water to give 170 mg (0.43 mmol, 60%) of 4 as white crystals: m.p. 186°–188° C.

$^1$H NMR (DMSO-d$_6$) 2.37 (3H, s), 3.4–3.7 (9H,m), 4.6 (1H,br), 4.7 (1H,br), 5.0 (1H, d), 5.3 (1H,br), 7.0 (2H, m), 7.7 (1H, m).

TLC: Silica gel, acetone:20 mM NaOAc 9:1, R$_f$=0.7.

d) 7-(β-galactosyl)-4-methylcoumarin-3-acetamidobiocytin (5)

To a stirred solution of 7-(β-galactosyl)-4-methylcoumarin-3-acetic acid (4) (146 mg, 0.368 mmol) in DMF (3 mL) was added N-hydroxysuccinimide (46 mg, 0.400 mmol) and 1-(3-dimethylaminopropyl)-3-ethylcarbodiimide hydrochloride (74 mg, 0.386 mmol). The solution was stirred at room temperature for 2.5 hours and added dropwise to a solution of biocytin (250 mg, 0.671 mmol) in 0.1M NaHCO$_3$ (5 mL) and DMF (1 mn) and stirred at room temperature for 2 hours. The solution was evaporated to dryness under reduced pressure and the residue was washed with hot methanol (3×10 mL). The methanol washes were evaporated to give an off white solid which was dissolved in water (3 mL) and purified by preparative EPLC (4×0.75 mL Injections) on ZORBAX C8 (4.6 mm×25 cm) eluting with a linear gradient of 5–15% acetonitrile in 0.1M triethylammonium acetate pH=7 at 2 mL/min. The desired product eluted at the end of the gradient as a single peak which was collected, evaporated, stripped from water (3×5 mL) to give 54 mg (0.07 mmol, 20%) of 5 as a white solid.

$^1$H NMR (DMSO-d$_6$) contains peaks which correspond to biocytin and 7-(β-galactosyl)-4-methylcoumarin-3-acetic acid.

TLC: Silica gel, methanol, R$_f$=0.7

Figure 6:
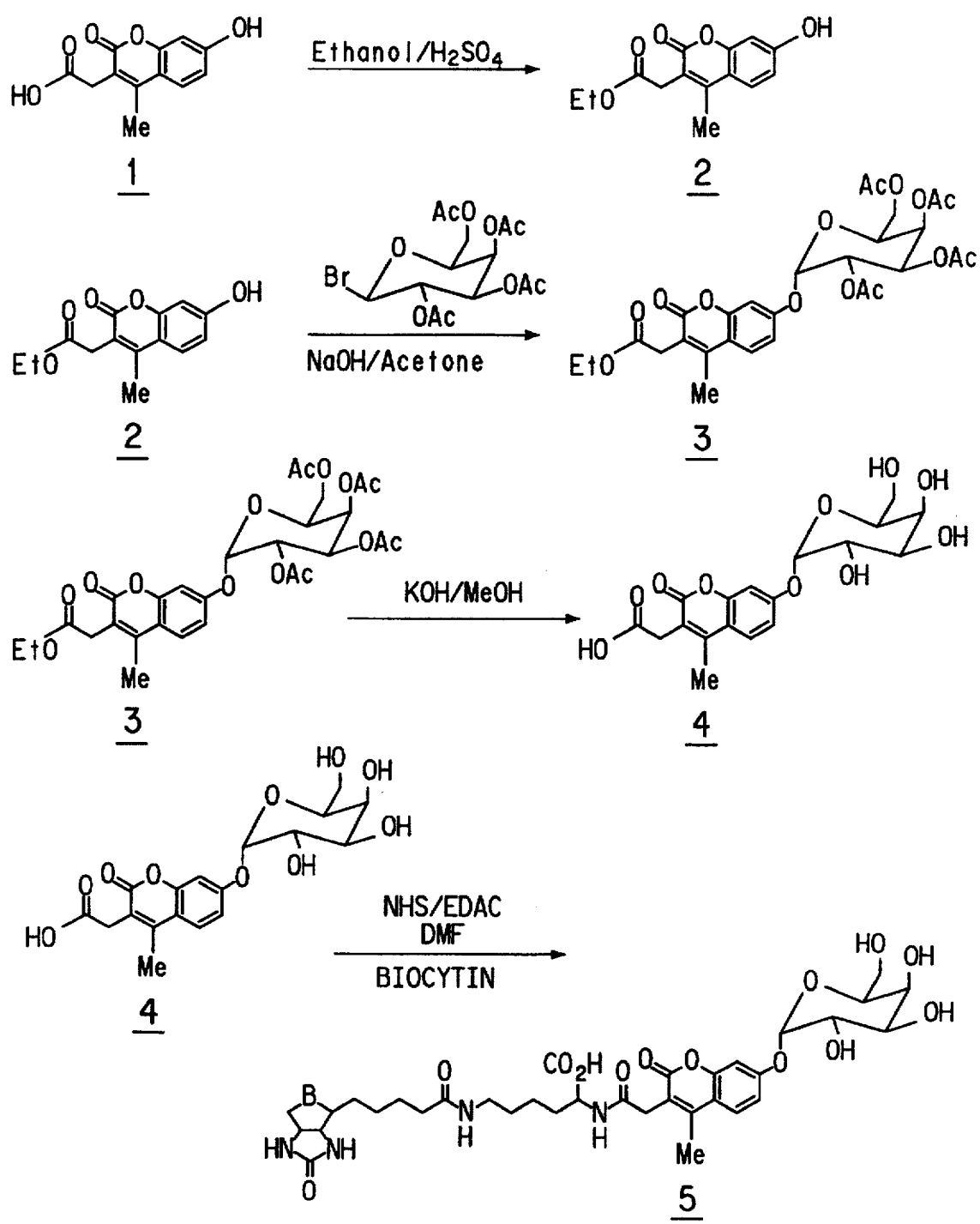
FIG. 6 depicts the synthesis of 7-(β-galactosyl)-4-methylcoumarin-3-acetamidobiocytin.

The synthesis of this compound is illustrated in FIG. 6.

EXAMPLE 11

Amplification Using a β-Galactosidase ADEAS

The preparation of 7-(β-galactosyl)-4-methylcoumarin-3-acetamidobiocytin (GCB) was described in Example 10 above.

Monoclonal antibodies were prepared by immunizing mice with a 7-hydroxy-4-methylcoumarin-3-acetic acid-BSA conjugate which was synthesized by reacting 7-hydroxy-4-methylcoumarin-3-acetic acid, succinimidyl ester (Molecular Probes, Eugene, Oreg.) with BSA. Hybridomas were produced by fusion of lymph node lymphocytes (Mirza, I. H. et al., J. Immunol. Methods 105, 235–243, 1987) by the method of de St. Groth, F. et al., J. Immunol. Methods 35, 1, 1980.

The assay was performed as follows: Polystyrene EIA strips (NUNC) were coated with goat anti-mouse IgG (Fc fragment specific) antibody (ICN) in 0.1M carbonate buffer pH 9.6, overnight at RT. The strips were then blocked with 2% BSA in PBS. After washing with PBST, the above-identified hydridoma supernatant diluted ⅕ in 1% BSA-PBST was incubated with the strips for 2 hr at RT. The strips were washed again. β-Galactosidase at concentrations ranging from 0.01 to 50 ng/ml (plus a 0 ng/ml blank) in 10 mM sodium phosphate, 1 mM MgCl$_2$, 0.1% BSA, pH 7.0 was added to the wells with either o-nitrophenyl-β-D-galactoside (ONPG) at 1 mg/ml (for colorimetric detection of β-galactosidase activity without amplification) or GCB at 100 ng/ml (for amplification) for 30 min at RT. The absorbance in the wells containing ONPG was read at 405 nm. The wells containing GCB were washed with PBST, and incubated with streptavidin-HRP for 15 min at RT. Following washing with PBST, the HRP substrate tetramethylbenzidine (SOMA Labs, Romeo, Mich.) was added for 30 min at RT, the reaction stopped with 3N H$_2$SO$_4$/1N HCl, and the absorbance at 450 nm determined.

Results

Figure 7:
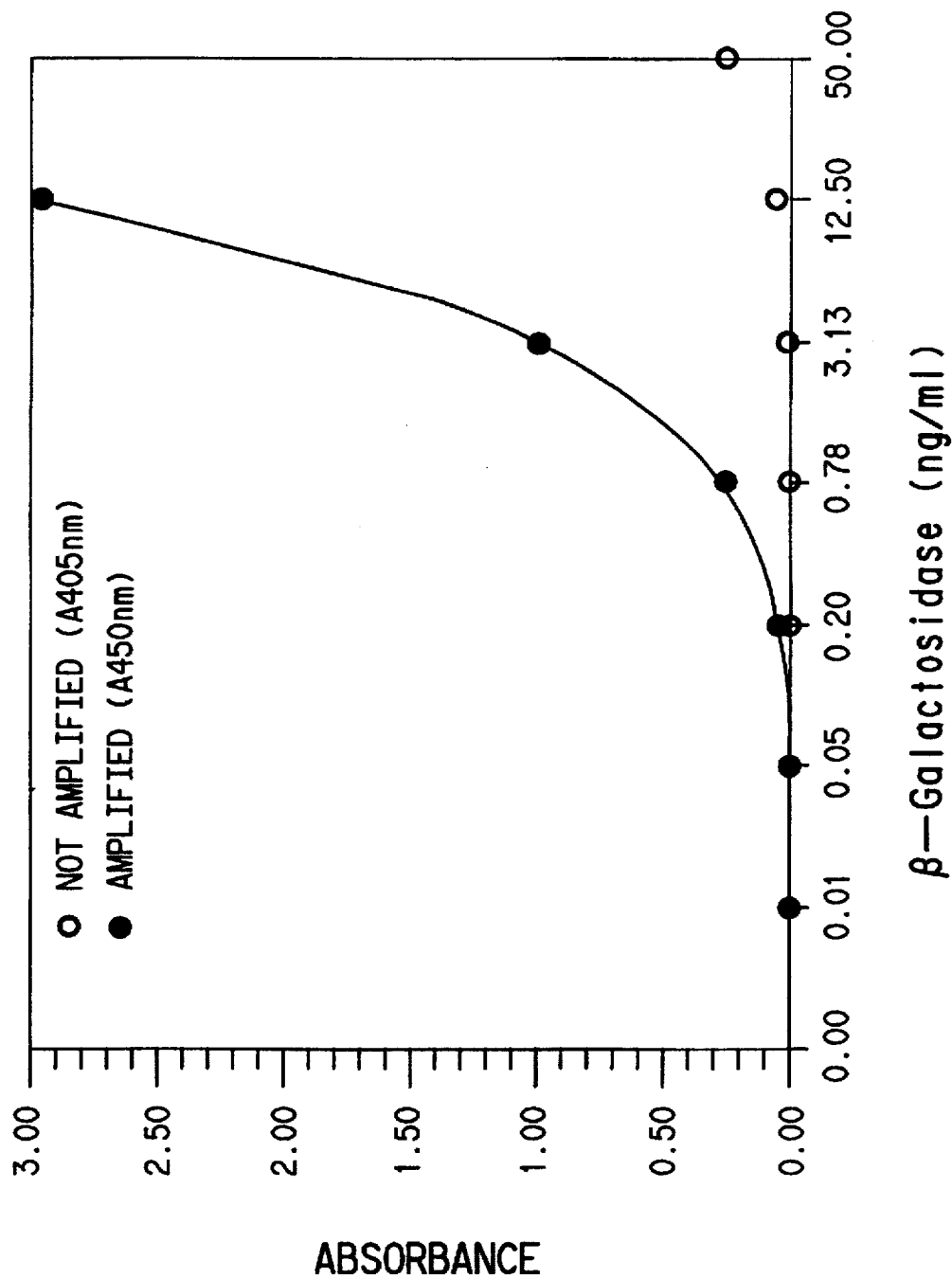
FIG. 7 is a graph comparing the results obtained in detecting a β-galactosidase ADEAS using a conventional, non-amplified assay format versus results obtained in detecting a β-galactosidase ADEAS using catalyzed reporter deposition to amplify the detector signal.

The results are shown in FIG. 7. The net absorbance (blank subtracted) is plotted vs. the β-galactosidase concentration. A 64-fold improvement in β-galactosidase detection was obtained using the catalyzed reporter deposition amplification method when compared to direct colorimetric detection.

What is claimed is:

1. A conjugate comprising a detectably labeled phenol.

2. A conjugate according to claim 1 wherein the detectable label is selected from the group consisting of a fluorescent label or a member of a specific binding pair.

3. A conjugate according to claim 2 wherein the detectable label is fluorescein, tetramethyl rhodamine, coumarin or biotin.

4. A method for the detection or quantitation of an analyte in an assay which comprises using an analyte dependent enzyme activation system comprising at least one enzyme to react with a conjugate consisting of a delectably labeled substrate specific for the enzyme system to form an activated conjugate which covalently deposits substantially wherever at least one receptor for the activated conjugate is immobilized, said receptor not being reactive with the analyte dependent enzyme activation system, wherein deposited detectable labels either directly or indirectly generate a signal which can be detected or quanititated.

5. A method according to claim 4 wherein at least one enzyme of the analyte dependent enzyme activation system is selected from the group consisting of oxidoreductases, hydrolases, lyases, transferases, isomerases, and ligases.

6. A method according to claim 5 wherein the enzyme is selected from the group consisting of peroxidases, oxidases, phosphatases, esterases and glycosidases.

7. A method according to claim 6 wherein the enzyme selected from the group consisting of horseradish peroxidase, glucose oxidase, alkaline phosphatase and beta-galactosidase.

8. A method according to claim 7 wherein the enzyme is horseradish peroxidase.

9. A method according to claim 8 wherein the conjugate is selected from the group consisting of biotin tyramine, p-hydroxyphenylpropionylbiocytin, or fluorescein tyramine.

10. A method according to claim 4 wherein the conjugate is reacted with detectably labeled antibody.

11. A method according to claim 4 wherein the conjugate is reacted with a detectably labeled member of a specific binding pair.

12. A method according to claim 4 wherein the conjugate is reacted with delectably labeled streptavidin.

13. A method according to claim 4 wherein the detectable label is selected from the group consisting of enzymes, radioactive isotopes, fluorogenic, chemiluminescent, or electrochemical materials or a member of a specific binding pair.

14. A method for producing an activated conjugate comprising reacting a peroxidase enzymo with a delectably labeled phenol.

15. A method according to claim 14 wherein the detectable label is selected from the group consisting of a fluorescent label and a member of a specific binding pair.

16. A method according to claim 15 wherein the detectable label is fluorescein, tetramethyl rhodamine, coumarin or biotin.

* * * * *